United States Patent [19]
Langford

[11] Patent Number: 5,277,868
[45] Date of Patent: Jan. 11, 1994

[54] SYRINGE DESTRUCTION DEVICE

[76] Inventor: Terrence R. Langford, 4049 Quiet Moon Dr., Tucson, Ariz. 85718

[21] Appl. No.: 957,722

[22] Filed: Oct. 6, 1992

[51] Int. Cl.⁵ .............................................. A61L 2/00
[52] U.S. Cl. .................................... 422/21; 422/22; 422/307; 422/308; 422/309; 206/366
[58] Field of Search .................. 422/21, 22, 307, 308, 422/309; 206/364–365, 366, 370

[56] References Cited

U.S. PATENT DOCUMENTS

| | | | |
|---|---|---|---|
| 4,452,358 | 6/1984 | Simpson | 206/366 |
| 4,488,643 | 12/1984 | Pepper | 206/366 |
| 4,862,573 | 9/1989 | Kelson et al. | 206/366 X |
| 4,900,500 | 2/1990 | Honeycutt | 264/263 |
| 4,989,307 | 2/1991 | Sharpe et al. | 206/366 X |
| 5,003,892 | 4/1991 | Bricken | 110/346 |
| 5,031,767 | 7/1991 | Bruno | 206/370 |
| 5,046,612 | 9/1991 | Mostarda et al. | 206/365 |
| 5,046,614 | 9/1991 | Torres et al. | 206/366 |
| 5,057,656 | 10/1991 | Galber | 206/366 |
| 5,067,223 | 11/1991 | Bruno | 29/426.5 |
| 5,069,667 | 12/1991 | Freundlich et al. | 604/110 |
| 5,085,338 | 2/1992 | Inagaki | 220/254 |
| 5,092,462 | 3/1992 | Sagstetter et al. | 205/366 |
| 5,106,594 | 4/1992 | Held et al. | 422/292 |
| 5,138,125 | 8/1992 | Salesses | 219/68 |
| 5,166,488 | 11/1992 | Peppard | 241/65 X |

FOREIGN PATENT DOCUMENTS 7900239  5/1979  World Int. Prop. O. .

Primary Examiner—Robert J. Warden
Assistant Examiner—Krisanne M. Thornton
Attorney, Agent, or Firm—Ogram & Teplitz

[57] ABSTRACT

A simple to use, single quantity, syringe sterilization and destruction device is disclosed. A syringe is inserted into the device needle first by the operator. The device grips the syringe and holds it in place. The device heats the steel needle portion of a syringe to sterilize the needle portion. The heat also melts the steel-to-plastic fitting between the steel needle portion and the plastic barrel portion of the syringe. The plastic barrel portion separates from the heated needle portion of the syringe by force of gravity or by a light pulling force exerted by a pulling mechanism. The hole in the fitting is sealed by the molten plastic. Sealing the hole maintains the integrity of the plastic barrel/plunger container and prevents spillage of contaminated waste. The heated needle is bent into a spiral bundle so that no sharp portions protrude from the spiral bundle. The spiral bundle is deposited into a container for recycling or waste disposal. The plastic barrel/plunger portion is placed into a microwave oven and heated until sterile. In an alternate embodiment the barrel/plunger portion is heated in the microwave oven until the plastic barrel/plunger portion is melted. The needles and plastic barrel/plungers are now sterile and safe. Both the needle and barrel/plunger waste can be disposed of safely or recycled.

32 Claims, 2 Drawing Sheets

SYRINGE DESTRUCTION DEVICE

BACKGROUND OF INVENTION

This invention relates generally to medical waste disposal and more specifically to the sterilization and disposal of contaminated syringes.

Syringes are commonly used in many environments including hospitals, doctors offices, dentists offices, and even at home by diabetics or others who require at-home hypodermic injections. The typical syringe consists of a hollow steel needle threadably coupled to a plastic barrel. A plastic plunger with a rubber gasket is inserted into the barrel for forcing fluids into and out of the plastic barrel and needle. Syringes are used to inject fluids into a body and to remove fluids from a body.

Syringes have always posed health and safety dangers. The sharp needles can stab a person accidentally, even when they are using the utmost care. The contaminated syringes can infect personnel through a needle wound or from spillage of their contaminated contents.

Today, however, the need for safe disposal of syringes is more important than ever. Serious and deadly diseases such as A.I.D.S. and hepatitis can be transmitted by a single needle injury. Often it is not known whether a patient is infected with a serious disease, thus causing fear and concern about all syringes.

The needle portion of a syringe poses two health and safety dangers. First, the needles are sharp and can cause a severe injury. When disposed of, the needles can puncture a waste container or bag and injure unsuspecting personnel. Waste disposal personnel can be injured by needles protruding from plastic garbage bags or from other inadequate waste disposal containers. Even after disposal, sharp needles poses a danger since they have been known to wash up on beaches or turn up in other public places.

Second, needles can pass on diseases, many of them very serious. Many diseases are highly infectious and contagious. A single needle prick from a contaminated needle can infect a person with one of these diseases. Some infectious diseases can be passed to personnel without even a needle prick, mere contact with the needle may be enough. The needles pose a health and safety threat until they have been completely neutralized by sterilization and by disabling the sharp portions.

Syringes pose a health and safety threat even after the needle has been removed. The barrel/plunger portion of the syringe often contains fluids contaminated with infectious diseases. The contaminated fluid in the barrel/plunger portion can leak or spill, thus spreading the disease. This can cause infection of medical personnel, patients, waste disposal personnel and others who come in contact with this waste. After final disposal of the syringe, the contaminated fluids can leak into the ground and contaminate ground water. The barrel/plunger portion of syringes pose a health and safety threat until they have been completely sterilized.

Many devices for disposal of syringes are known. However, they are all lacking in one or more ways.

U.S. Pat. No. 5,003,892 issued to Bricken on Apr. 2, 1991 discloses a process for the sterile disposal of syringes. The Bricken process places used syringes into a container and heats the syringes until the melted plastic encapsulates the needles thus sterilizing and neutralizing the needles at the same time. This process, however, is not practical for disposal of syringes one at a time. It does not prevent spillage of infectious material when syringes are placed into the container nor does it provide for disassembly and sterilization of parts contaminated by such spillage. Finally, it does not provide a means for collecting noxious fumes produced from the process.

U.S. Pat. No. 5,106,594 issued to Held et al. on Apr. 21, 1992 shows an apparatus and method for disintegrating a wide variety of medical wastes and disinfecting them with radio waves. The large scale and complexity of this device restricts its use to large bulk processing of medical wastes. Also, waste products remain in their infectious and dangerous state while waiting for processing.

U S. Pat. No. 4,900,500 issued to Honeycutt on Feb. 13, 1990 teaches a process of sterilizing and immobilizing potentially infectious devices by means of enveloping them within a hardening polymer that thermally sterilizes the contents by means of an exothermic polymerization reaction. This is essentially bulk processing and requires storage of hazardous waste while enough waste for a batch is accumulated. The process is time consuming, odor causing, and the enclosing polymer will ultimately decompose.

There are numerous other U.S. patents for syringe disposal devices. Most are lacking in one or more respects. Many do not sterilize the infectious waste, others do not disable the sharp needles, still others only process wastes in bulk. Finally, some are complicated, dangerous to use, or give off noxious odors.

Clearly, there exists a need for an improved syringe disposal device which is on-site, simple to use, processes single syringes, provides immediate sterilization, and disables the sharp needles.

SUMMARY OF INVENTION

This invention creates a simple to use, single quantity, syringe sterilization and destruction device. The device heats the steel needle portion of a syringe to sterilize the needle portion. The heat melts the steel-to-plastic fitting between the steel needle portion and the plastic barrel portion of the syringe. The barrel portion separates from the needle portion of the syringe by force of gravity or by a light pulling force exerted by a pulling mechanism. The hole in the fitting is sealed by the molten plastic. Sealing the hole maintains the integrity of the barrel/plunger container and prevents spillage of contaminated waste. The heated needle is bent into a spiral bundle so that no sharp portions protrude from the spiral bundle. The spiral bundle is deposited into a container for recycling or disposal. The barrel/plunger portion is placed into a microwave oven and heated until sterile.

In an alternate embodiment the barrel/plunger portion is heated in the microwave oven until the plastic barrel/plunger portion is melted.

The needles and barrel/plungers are now sterile and safe. Both the needle and barrel/plunger waste can be disposed of safely or recycled.

The device is simple to use, can process single syringes, and is small enough for use in a small medical office, at home, or anywhere syringes are used.

The first step in using the device is to insert the syringe into the device. The syringe is inserted into the device needle first. The preferred embodiment provides a loader tray to hold the syringe, aid the user in inserting the syringe into the device, and to catch any spillage of contaminated waste. The device grips and holds the syringe and activates the sterilization and needle disabling process.

In the preferred embodiment, the gripping means holds the syringe at the base of the needle portion where the plastic barrel portion and needle portion are attached.

The needle portion is heated to sterilize the needle and to assist the separation of the needle from the barrel portion of the needle. The preferred embodiment uses simple induction heating to heat the needle. The needle is heated to a sufficient temperature and for a sufficient time to completely sterilize the needle. As the needle is heated above the melting point of the plastic barrel portion, the plastic barrel portion separates from the needle portion and drops into the loader tray.

When the plastic barrel separates from the needle, the hole created in the plastic barrel is conveniently sealed by the molten plastic. This seals the barrel/plunger assembly thus preventing spills and leaks of contaminated waste.

The sterilized needle is then bent to disable the sharp portion of the needle. The preferred embodiment rolls the needle into a spiral bundle with the sharp end of the needle at the center of the bundle and the threaded end pressed flat against the spiral bundle. Those of ordinary skill in the art readily see other bending configurations that achieve the objective of disabling the sharp portion of the needle.

The sterilized needle bundle is dropped into a container where it is safely stored until disposal or recycling. The needle in completely safe at this time since it has been sterilized and the sharp portion has been disabled.

The plastic barrel/plunger portion is dropped into a microwave oven. The preferred embodiment provides a container to hold the barrel/plungers in the center portion of the microwave oven. This eliminates the chance of a barrel/plunger falling into a "shadow" area of the oven where the microwave energy is less intense and enhances the effectiveness of the microwave sterilization.

The operator closes the door and turns on the microwave oven. The oven operates at a sufficient power level and for a sufficient time to sterilize the barrel/plungers and any waste contained inside them. In an alternate embodiment, the barrel/plungers area heated until they are melted, creating a block of sterilized plastic.

When the process is completed, the syringe is sterilized and the needle is disabled. The steel needles and plastic barrel/plungers are no longer hazardous wastes and can be disposed of as normal waste or recycled.

DETAILED DESCRIPTION OF THE DRAWINGS

Figure 1:
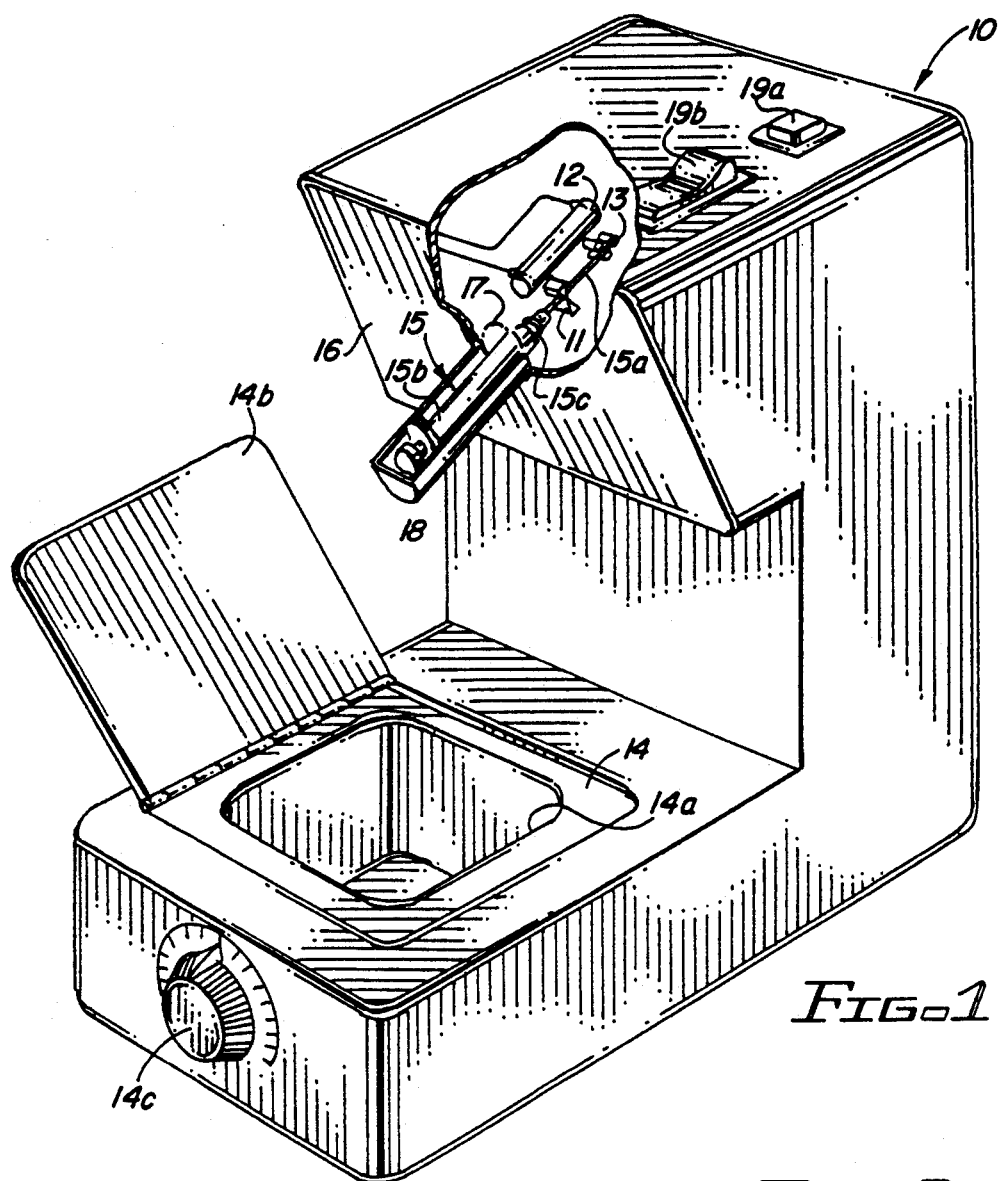
FIG. 1 is a perspective view of the preferred embodiment of the invention.

FIG. 1 is a perspective view of the preferred embodiment of the invention.

The housing 10 encloses the needle gripping means 11, heater 12, needle bending means 13, and microwave oven 14.

The contaminated syringe 15 is inserted into the device 16 through opening 17. The syringe 15 is inserted needle first. The insertion is aided by loader tray 18. The loader tray 18 precludes operator error during insertion and catches any spillage of contaminated waste when the syringe 15 in inserted into the device 16.

In the preferred embodiment, syringe 15 is inserted at a slightly upward angle so the barrel/plunger portion 15b is lower than the needle 15a. This angle aids in the separation of the barrel 15b from the needle 15a as described below.

Insertion of syringe 15 actives gripping means 11 which hold the syringe 15 in the device 16. Those of ordinary skill in the art readily see various embodiments of gripping means to hold a needle.

The heater 12 begins heating the steel needle 15a. The preferred embodiment uses low frequency electromagnetic induction heating to heat the needle 15a. Those of ordinary skill in the art readily see alternate methods that can be employed to heat the needle 15a. These include, but are not limited to, high frequency induction heating, electric radiant heat, gas flame, microwave radiation, and radio waves.

Heater 12 heats needle 15a to a sufficient temperature and for a sufficient time to completely sterilize the needle 15a. Heater 12 also heats the needle 15a to a sufficient temperature to melt the plastic fitting 15c between the barrel 15b and the needle 15a. As the plastic fitting 15c melts, gravity pulls the barrel 15b from the needle 15a. When barrel 15b separates from needle 15a, barrel 15b and plunger 15d drop into loader tray 18.

The hole created by the separation of barrel 15b and needle 15a is sealed by the molten plastic. Sealing the barrel 15b and plunger 15d assembly serves the dual purpose of preventing spillage and providing a secondary sealed container for the enclosed contaminated waste.

In an alternate embodiment, the loader tray 18 is not used, thus allowing the barrel 15b and plunger 15d to fall directly into the microwave oven 14.

The sterilized needle 15a is bent by bending means 13 to disable the sharp portion of the needle 15a. The preferred embodiment bends the needle 15a into a flat spiral bundle. The sharp portion of the needle 15a is in the center of the bundle and therefore rendered harmless. The bending process is accomplished with a simple gripping/bending device 13. The gripping/bending device grabs the sharp portion of the needle 15a and rolls the needle 15a into a spiral. The threaded end of the needle 15a is pressed flat against the spiral bundle to further eliminate any sharp edges. Those of ordinary skill in the art readily see other bending configurations and other bending devices which accomplish similar results.

When the sterilization and bending processes are complete, the needle bundle is dropped into a needle container (not shown) for storage until it can be disposed of.

The still contaminated barrel 15b and plunger 15d are in the loader tray 18. The loader tray 18 is removed from the device 16 and the barrel 15b and plunger 15d are dropped into the microwave oven 14. Loader tray 18 is readily washable and is ordinarily not contaminated since the needle is laid on the loader tray 18 with its tip upward.

The preferred embodiment provides a microwaveable container 14a to hold the barrels 15b and plungers 15d in the microwave oven 14. The container 14a holds the barrel/plungers 15b in the center portion of the microwave oven 14. This prevents a barrel 15b and plunger 15d assemblies from dropping into a corner of the microwave oven where there may be "shadows" and the microwave energy may be less intense.

The barrel 15b and plunger 15d are sterilized by microwaves from microwave oven 14. The operator closes oven door 14b and turns on the microwave oven 14 via timer 14c. In the preferred embodiment, microwave oven 14 heats the barrel 15b and plunger 15d to a sufficient temperature and for a sufficient time to sterilize the barrel 15b and plunger 15d.

The microwave oven 14 can be cycled after each syringe is disposed of, or the operator can wait until several barrels 15b and plungers 15d need to be sterilize.

In an alternate embodiment, the barrel 15b and plunger 15d are heated to a temperature sufficient to melt the plastic. This creates a sterile block of plastic which is ready for disposal or recycling.

Those of ordinary skill in the art can readily see that other similar sterilization means may be employed to achieve the sterilization. These include, but are not limited to, electromagnetic fields, radio frequency waves, and the like. Switch 19a controls power to device 16. Light 19b indicates when power is being supplied to device 16.

Figure 2:
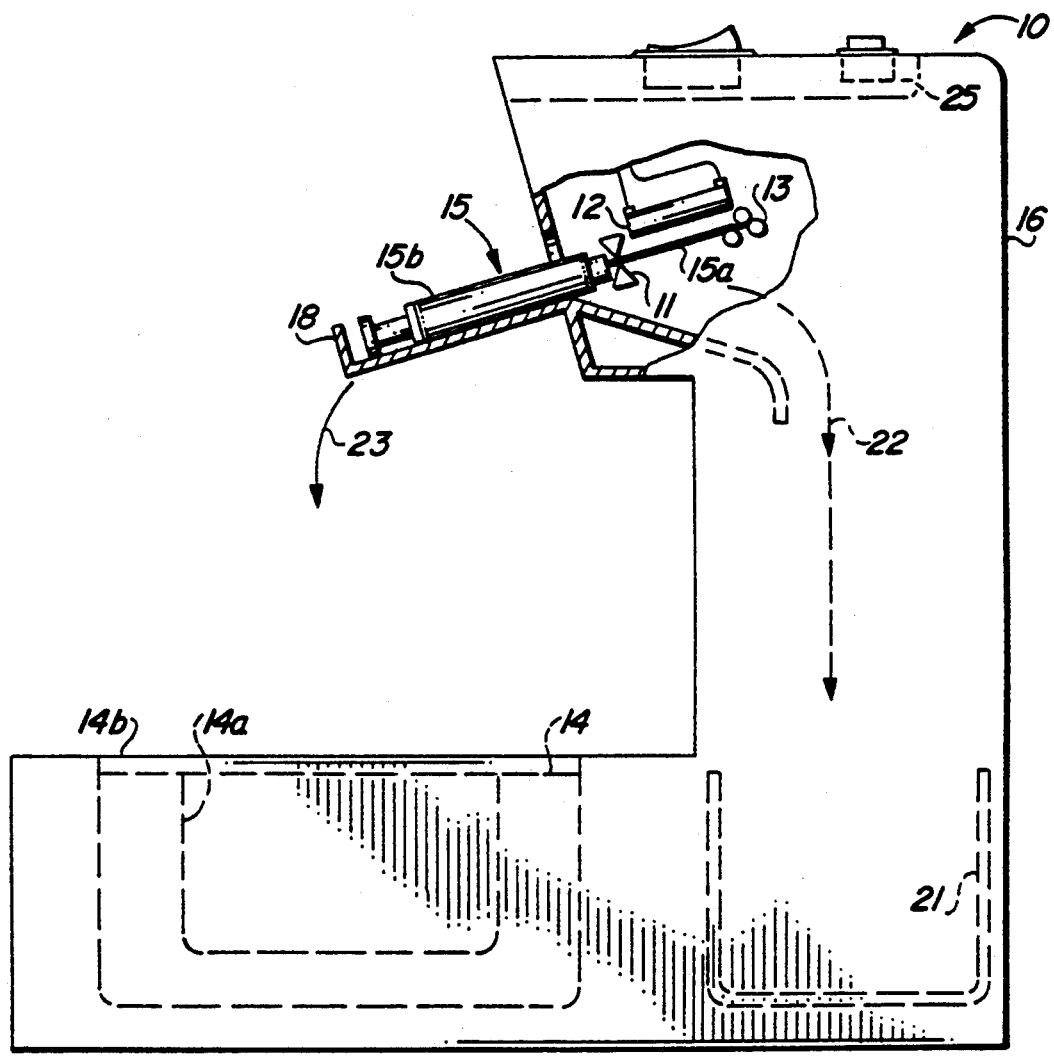
FIG. 2 is a side view of the preferred embodiment of the invention.

FIG. 2 is a side view of the preferred embodiment of the invention.

Syringe 15 is placed into loader tray 18. Loader tray 18 aids the user in inserting syringe 15 into the device 16. Tray 18 precludes operator error and catches any accidental spillage upon introduction of syringe 15 into the device 16. Loader tray 18 is removable for easy cleaning.

Needle 15a is held by gripping means 11. Heater 12 heats needle 15a to a sufficient temperature and for a sufficient time to sterilize needle 15a and to melt the plastic fitting between needle 15a and plastic barrel 15b.

The small effusion of vapor from the heating process is absorbed by canister 25. Canister 25 contains activated charcoal or a similar substance to absorb the vapors. Canister 25 is removable for periodic replacement.

By the force of gravity, plastic barrel 15b separates from needle 15a when the fitting 15c is sufficiently melted. As the separation occurs, the molten plastic seals the hole left by the removal of needle 15a.

The bending means 13 bends the needle 15a such that the sharp portion of the needle 15a is disabled. The preferred embodiment rolls the needle 15a into a flat spiral with the sharp portion at the center and the threaded end pressed flat against the spiral bundle. After the bending operation, needle 15a is safe for disposal. The needle 15a is sterile and has no sharp portions. The spiral needle bundle is dropped into a container 21, as shown by arrows 22, for temporary storage.

The barrel portion 15b is resting in the loader tray 18 after separation from the needle 15a. The operator removes the loader tray 18 from the device 16 and dumps the barrel 15b and plunger 15d into the microwave oven 14.

In an alternate embodiment, the loader tray 18 is not used. The syringe 15 is placed directly into the device 16. When the barrel 15b separates from the needle 15a, the barrel 15b and plunger 15d drop directly into the microwave oven as shown by arrow 23.

A container 14a is located inside the microwave oven 14 to receive the barrel 15b and plunger 15d. Container 14a holds the barrel 15b and plunger 15d in the center portion of the microwave oven 14. This assures that the barrel 15b and plunger 15d do not fall into a corner of the microwave oven 14 and that they are fully exposed to the microwaves (not shown).

Figure 3:
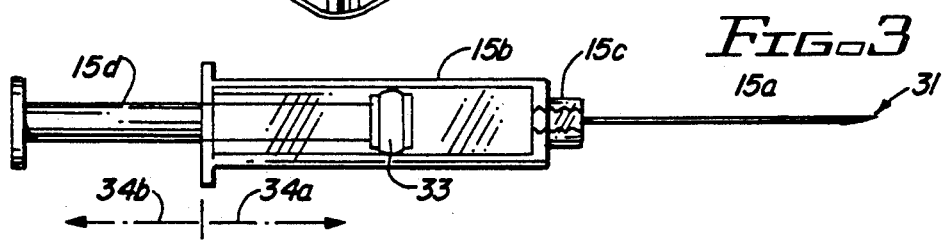
FIG. 3 is a side view of a syringe.

FIG. 3 is a side view of a typical syringe.

The hollow steel needle portion 15a is threadably attached to the plastic barrel 15b via fitting 15c. The sharp portion is in indicated by arrow 31. Plunger 15d extends into the interior of barrel 15b. Plunger 15d has a rubber gasket 33 to create a seal against the interior of barrel 15b. Plunger 15d is moveable by an operator as shown by arrows 34a and 34b. Actuation of plunger 15d, as shown by arrow 34a, propels fluid from the interior of barrel 15b, thru the hollow steal needle 15a and out the sharp portion of the needle 15a.

Figure 4A:
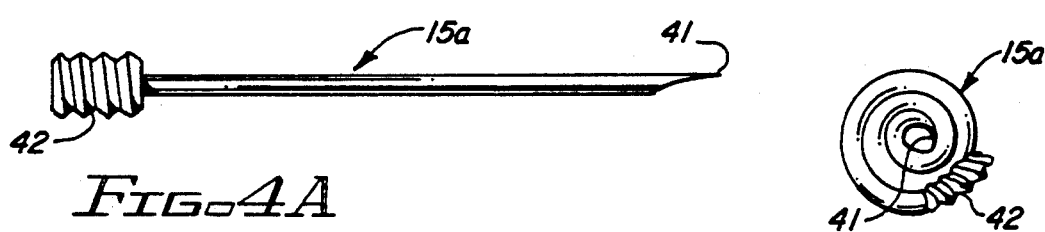
FIG. 4a is a needle portion of a syringe.

FIG. 4a shows a needle portion of a syringe before it is bent. The sharp portion 41 is dangerous and must be disabled. The threaded portion 42 may also have sharp edges and also must be disabled.

Figure 4B:
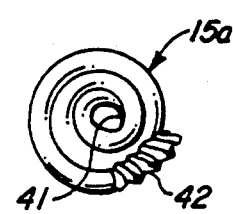
FIG. 4b is a needle portion of a syringe after it is bent into a spiral bundle by the invention.

FIG. 4b shows a needle portion of a syringe after it is bent into a flat spiral bundle.

This figure shows the preferred bending configuration. Needle 15a is bent into a flat spiral. The sharp portion 41 is at the center of the spiral. The sharp portion 41 does not protrude from the bundle and is safe. The threaded portion 42 is pressed tightly against the perifery of the spiral bundle to further eliminate any sharp edges.

It is clear from the foregoing that the present invention represents a new and useful apparatus for the sterile and safe destruction of syringes at the point of use.

What is claimed is:

1. A syringe destruct apparatus comprising:
   a) a housing having,
      1) a gripping means located in said housing for holding a needle portion of a syringe in said housing, and,
      2) a heating means located in said housing for heating said needle portion to a temperature sufficient to sterilize said needle; and
   b) a microwave oven located beneath said gripping means to receive a barrel/plunger portion of said syringe.

2. The syringe destruct apparatus according to claim 1 further comprising needle bending means located in said housing for creating a waste bundle from a heated needle portion of said syringe such that sharp portions do not protrude from said waste bundle.

3. The syringe destruct apparatus according to claim 2 wherein said needle bending means includes means for creating a spiral from said heated needle portion.

4. The syringe destruct apparatus according to claim 3 further comprising a needle disposal container in said housing to receive and hold said waste bundle.

5. The syringe destruct apparatus according to claim 4 further including pulling means located in said housing for separating said needle portion from said barrel/plunger portion.

6. The syringe destruct apparatus according to claim 5 further comprising a cage means positioned inside said microwave oven, a) for catching said barrel/plunger as it falls from said gripping means; and, b) for holding said barrel/plunger in a central portion of said microwave oven.

7. The syringe destruct apparatus according to claim 6 wherein said microwave oven is located in said housing.

8. The syringe destruct apparatus according to claim 7 further comprising vapor absorption means for absorbing vapor and fumes from said housing, said vapor absorption means operatively connected to said housing.

9. The syringe destruct apparatus according to claim 8 further comprising a loader tray means attached to said housing, said loader tray means for supporting said syringe and catching any spilled fluids from said syringe.

10. The syringe destruct apparatus according to claim 9 wherein said loader tray means is removable from said housing.

11. A needle destruction apparatus comprising:
a) a gripping means for holding a needle portion of a syringe; and,
b) a heating means for heating the needle portion to a temperature sufficient to sterilize said needle portion.

12. The needle destruction apparatus according to claim 11 further comprising a housing enclosing said gripping means and said heating means.

13. The needle destruction apparatus according to claim 12 further comprising needle bending means located in said housing for creating a waste bundle from a heated needle portion of said syringe such that sharp portions do not protrude from said bundle.

14. The needle destruction apparatus according to claim 13 wherein said needle bending means includes means for creating a spiral from said heated needle portion.

15. The needle destruction apparatus according to claim 13 further including pulling means located in said housing for separating said needle portion from said barrel/plunger portion.

16. The needle destruction apparatus according to claim 15 further comprising a needle disposal container in said housing to receive and hold said waste bundle.

17. The needle destruction apparatus according to claim 16 further comprising a loader tray means attached to said housing, said loader tray means for supporting said syringe and catching any spilled fluids from said syringe.

18. The needle destruction apparatus according to claim 17 wherein said loader tray is removable from said housing.

19. The needle destruction apparatus according to claim 18 further comprising a microwave oven located beneath said gripping means to receive a barrel/plunger portion of said syringe.

20. The needle destruction apparatus according to claim 19 further comprising a support means positioned inside said microwave oven,
a) for catching said barrel/plunger as it falls from said gripping means; and,
b) for holding said barrel/plunger in a center portion of said microwave oven.

21. The needle destruction apparatus according to claim 20 wherein said microwave oven is located in said housing.

22. The needle destruction apparatus according to claim 21 further comprising fume absorption means located in said housing for absorbing fumes from said housing.

23. A syringe destruct device comprising:
a) a housing having,
1) a gripping means for holding a needle portion of a syringe at an inclined position within said housing,
2) a heating means for heating said needle portion,
3) a needle bending means for creating a spiral waste bundle from said needle portion such that sharp portions do not protrude from said bundle,
4) a pulling means for separating said needle portion from a barrel/plunger portion of said syringe,
5) a needle disposal container to receive and hold and spiral waste bundle, and,
6) a fume absorbing means for absorbing fumes from said housing;
a) a microwave oven located beneath said gripping means to receive said barrel/plunger;
c) a cage means positioned inside said microwave oven:
1) for catching said barrel/plunger as it falls from said gripping means, and,
2) for holding said barrel/plunger in a center portion of said microwave oven; and,
d) a loader tray attached to said housing, said loader tray supporting said syringe and catching any spilled fluids from said syringe.

24. The syringe destruct device according to claim 23 wherein said loader tray is removable from said housing.

25. The syringe destruct device according to claim 24 wherein said microwave oven is located in said housing.

26. A method of disposing of syringes comprising the steps of:
a) providing a gripping means for holding a syringe;
b) heating a needle portion of said syringe with sufficient heat to sterilize said needle;
c) separating said needle portion from a barrel/plunger portion of said syringe; and,
d) heating said barrel/plunger with microwaves to a temperature sufficient to sterilize said barrel/plunger portion.

27. The method of disposing of syringes according to claim 26 wherein the step of separating is followed by the step of bending said needle into a spiral waste bundle such that no sharp portions protrude from said spiral waste bundle.

28. The method of disposing of syringes according to claim 27 wherein the step of separating includes the step of pulling said heated needle from said barrel/plunger portion.

29. The method of disposing of syringes according to claim 27 wherein the step of separating includes unthreading said heated needle from said barrel/plunger portion.

30. The method of disposing of syringes according to claim 27 wherein the step of bending is followed by the step of providing a needle waste container and placing said spiral waste bundle into said needle waste container.

31. The method of disposing of syringes according to claim 27 wherein the step of heating said barrel/plunger is preceded by the steps of:
a) providing a barrel/plunger container;

b) placing said barrel/plunger portion into said container;
c) providing a microwave oven; and,
d) placing said barrel/plunger container in a center portion of said microwave oven.

32. The method of disposing of syringes according to claim 31 wherein the step of heating said barrel/plunger includes the step of heating said barrel/plunger to a temperature to melt a plastic portion of said barrel/plunger.

* * * * *